(12) United States Patent
Zimmermann et al.

(10) Patent No.: US 8,431,889 B2
(45) Date of Patent: Apr. 30, 2013

(54) METHOD AND DEVICE FOR REPETITIVE CHEMICAL ANALYSIS OF A GAS FLOW

(75) Inventors: Ralf Zimmermann, Bergisch Gladbach (DE); Mohammad Reza Saraji-Bozorgzad, Munich (DE); Markus Simon Eschner, Tapfheim (DE); Thomas Maximilian Groeger, Munich (DE)

(73) Assignee: Helmholtz Zentrum Muenchen Deutsches Forschungszentrum fuer Gesundheit und Umwelt (GmbH), Neuherberg (DE)

( * ) Notice: Subject to any disclaimer, the term of this patent is extended or adjusted under 35 U.S.C. 154(b) by 0 days.

(21) Appl. No.: 13/423,738

(22) Filed: Mar. 19, 2012

(65) Prior Publication Data

US 2012/0286154 A1 Nov. 15, 2012

Related U.S. Application Data

(63) Continuation of application No. PCT/EP2010/063684, filed on Sep. 17, 2010.

(60) Provisional application No. 61/243,764, filed on Sep. 18, 2009.

(30) Foreign Application Priority Data

Sep. 18, 2009 (EP) .................................. 09170744

(51) Int. Cl.
*H01J 49/04* (2006.01)
*H01J 47/02* (2006.01)

(52) U.S. Cl.
USPC ........ 250/288; 250/281; 250/282; 250/443.1; 73/23.22; 73/23.35

(58) Field of Classification Search .................. 250/288, 250/281, 282, 443.1; 73/23.22, 23.35
See application file for complete search history.

(56) References Cited

U.S. PATENT DOCUMENTS

| | | | | |
|---|---|---|---|---|
| 4,509,855 | A | * | 4/1985 | Gay ................................ 356/72 |
| 6,727,499 | B2 | * | 4/2004 | Zimmermann et al. ...... 250/288 |

(Continued)

FOREIGN PATENT DOCUMENTS

| | | |
|---|---|---|
| EP | 0 669 531 | 2/1995 |
| EP | 0 921 393 | 10/1998 |

(Continued)

OTHER PUBLICATIONS

Maeno et al., "Simple and versatile injection system for capillary gas chromatographic columns," Journal of Chromatography A, Science Direct, Cincinnati, Ohio. pp. 201-215 (1996).

(Continued)

*Primary Examiner* — Nikita Wells
(74) *Attorney, Agent, or Firm* — Jenkins, Wilson, Taylor & Hunt, P.A.

(57) ABSTRACT

The present invention relates to a method for repetitive chemical analysis of a gas flow, wherein said gas flow consists of a carrier gas and gaseous chemical compounds, comprising the following method steps: feeding said gas flow to a gas chromatographic separation column by means of a feeding device; collecting at least a part of said gaseous chemical compounds for a defined time period by means of a thermally based collecting device which is coupled to said gas chromatographic separation column and/or said feeding device; releasing said collected gaseous chemical compounds in a temporally focused manner by means of said thermally based collecting device; separating said released gaseous chemical compounds by means of said gas chromatographic separation column; and analyzing said separated gaseous chemical compounds by means of an analyzer. The present invention further relates to a device for performing such a method.

17 Claims, 9 Drawing Sheets

U.S. PATENT DOCUMENTS 7,309,377 B2 * 12/2007 Eriksen et al. .................. 95/82
2009/0039250 A1 2/2009 Ishimaru et al.

FOREIGN PATENT DOCUMENTS

JP          3220447      3/1991
WO       WO 01/51179    7/2001

OTHER PUBLICATIONS

Muhlberger et al., "Comprehensive On-Line Characterization of Complex Gas Mixtures by Quasi-Simultaneous Resonance-Enhanced Multiphoton Ionization, Vacuum-UV Single-Photon Ionization, and Electron Impact Ionization in a Time-of-Flight Mass Spectrometer: Setup and Instrument Characterization," Analytical Chemistry, American Chemical Society, vol. 76, No. 22, pp. 6753-6764 (2004).

Welthagen et al., "One-dimensional and comprehensive two-dimensional gas chromatography coupled to soft photo ionization time-of-flight mass spectrometry: A two-and three-dimensional separation approach," Journal of Chromatography A, Science Direct, pp. 54-61 (2007).

Adahchour et al., "Recent developments in the application of comprehensive two-dimensional gas chromatography," Journal of Chromatography A, Elsevier. HV, Amsterdam, The Netherlands. pp. 67-108.

Zimmermann et al., "An ultracompact photo-ionization time-of-flight mass spectrometer with a novel vacuum ultraviolet ligth source for on-line detection of organic trace compounds and as a detector for gas chromatography," The 4th International Conference on Combustion, pp. 24-31 (2008).

Zimmermann et al., "Photo-ionisation mass spectrometry as detection method for gas chromatography. Optical selectivity and multi-dimensional comprehensive separations," Journal of Chromatography A, Science Direct, pp. 296-308 (2008).

International Search Report for Application Serial No. WO 2011033054 dated Apr. 5, 2011.

* cited by examiner

METHOD AND DEVICE FOR REPETITIVE CHEMICAL ANALYSIS OF A GAS FLOW

CROSS-REFERENCE TO RELATED APPLICATIONS

This application is a continuation of and claims priority to PCT/EP2010/063684, filed Sep. 17, 2010, which claims the benefit of and priority to European Patent Application 09 170 744.8, filed Sep. 18, 2009, and of U.S. Provisional Application Ser. No. 61/243,764, filed Sep. 18, 2009, the entire disclosures of which are herein incorporated by reference.

FIELD OF THE INVENTION

The present invention relates to a method and a device for repetitive chemical analysis of a gas flow, in particular for comprehensive two-dimensional on-line analysis of chemical compounds.

BACKGROUND OF THE INVENTION

Thermal analysis (TA) like thermogravimetry (TG) represents an important sector of instrumental analysis for example in chemistry and industrial process controlling. TA is utilized to characterize temperature dependent material properties, to evaluate thermo dynamical conversions and/or thermophysical parameters, as well as to observe chemical reactions. But for more detailed and advanced applications often a chemical investigation of the evolved gases—evolved gas analysis (EGA)—is indispensable. Depending on the requirements, this EGA can be realized with sequentially working analytical devices like gas chromatographs (GC) or with on-line real-time analytical devices, e.g. mass spectrometers (MS). These approaches enable the investigation of chemical classes and species of the evolved molecules. The mass spectrometry method commonly used in conjunction with TG is quadrupole mass spectrometry (QMS) with electron ionization (EI). Generally, the currently available MS systems use electrons with a kinetic energy of 70 eV for electron impact ionization. Typically, EI mass spectra hardly contain molecular ion signals beside the dominating fragment peaks due to the excess energy of these electrons. These fragment signals are characteristic for different molecules and can be used for alignment as a so called finger print of species in conjunction with EI data bases in order to identify molecules and its chemical structure.

However, in case of samples like polymers, plastic blends, plastic copolymers and fossil fuels containing multiple organic compounds, fragment peaks overlap and complicate or even prevent identification of evolving original substances from the TG system. To overcome this problem, different approaches are known to the applicant and have been developed by several research groups in the past decades. One auspicious method is to couple TA with a separation technique, e.g. GC in combination with MS for EGA. Due to the separation technique, the analytes disperse along the GC-capillary and reach the ion source of the MS at different retention times. Consequently the number of simultaneously ionized compounds is reduced and therefore the EI caused fragments do not hinder identification. In case of Pyrolysis-GC-MS (Py-GC-MS), samples are pyrolyzed instantly and a narrow plug is transferred to the GC-MS, where it can be separated within only one GC run. This method however does not provide TA relevant signals, e.g. mass loss or information about the enthalpy of formation of the relevant sample. Furthermore, the reaction kinetics can be totally different from a continuously heated analysis of the sample. However, TA-GC-MS and temperature controlled Py-GC-MS are comparable due to its opportunities regarding the analysis of pyrolysis products in many cases. Due to the offline character of the GC technique, the assay is usually collected offline and analyzed separately with the GC-MS. This is associated with sample preparation and longer measurement periods and additionally, chemical reactions between products are not to be excluded upon subsequent sample handling (heating).

An online coupling of the TG-GC-MS can be realized using valve systems in combination with sample loops allowing a quasi continuous operation of the TG-GC-MS system. Although these systems can uniquely be used for high performance qualitative and quantitative EGA, which is often based on prior knowledge of the sample, only parts of the molecular composition are usually analyzed, while sample information during two GC runs get lost (heart cut technique).

Another promising way is using soft ionization methods, where fragmentation of organic molecules from EGA can be circumvented. MS with soft ionization provide mass spectra containing basically molecular ion peaks [M+] which are therefore clear and easy to interpret. First thermal decomposition measurements and pyrolysis studies using laser based photon ionization revealed that highly valuable molecular information on the thermal decomposition processes can be achieved. Since laser based instrumentation often involves big drawbacks, regarding the high costs and complexity of the laser devices, vacuum ultraviolet (VUV) lamps such as deuterium or krypton discharge and electron beam pumped excimer Lamps (EBEL) are an attractive option. In case of single photon ionization (SPI), only one photon with the energy $E_{hv}$ higher than the ionization energy EI of the relevant molecule can lead to ionization. Consequently, the photon energy determines selectivity and acts as an energetic threshold. Molecules with an EI less than $E_{hv}$ can be ionized without any regard to its structure and formation in contrast to resonance enhanced multi photon ionization (REMPI). Although SPI mass spectra mainly consist of molecular ion peaks, a correlation between mass information and molecular structure is impossible, if there is no information about the sample composition. Therefore, SPI as a quasi selective ionization method is not appropriate to differ between isobaric and isomeric molecules.

To improve the resolving power and the isobaric separation ability of an analytical device and therefore to achieve a clearer conclusion about a sample composition, two or more independent separating methods can be coupled inline. One of the widespread multi dimensional analysis (MDA) techniques is multi dimensional separation using two dimensional GC (GC–GC or GC×GC), where GC–GC represents the so called heart cut technique. Two different chromatographic capillaries are connected serially. Often valve systems are utilized between the two columns to extract fractions of interest and lead this fractions to the second column for further separation. GC×GC, which is a comprehensive hyphenation in contrast to GC–GC, uses modulators and a short second GC capillary (fast GC). The modulator acts as a device connected between the first and the second GC-column to focus and to re-inject the eluents from the first into the second column. The choice of the type and length of the second column as well as the modulator type and modulation time is thereby crucial for the best achievable separation power. Single photon ionization mass spectroscopy (SPIMS) with its soft ionization character acts also as a separation technique. Therefore GC×GC in its essential principles closely resembles GC×SPIMS. In both, the samples components are dispersed in time by the GC and are lead to the secondary analytical device either individually or at least in greatly simplified sub-mixtures. Where the first GC creates a primary retention time axis, the second instrument with its own resolving power operates as a detector for the inlet GC and provides an independent analysis of the dispersed sample eluting from the primary GC. GC×GC as well as GC×SPIMS combine independent analytical techniques and generate comprehensive two dimensional data sets. In case of GC×GC, the two dimensions are given by the two different retention time axes and each substance is defined by its specific location in the separation plane. Sample constituents investigated with GC×SPIMS are also defined by one specific location in its dimensions, which is determined by its retention time in the first and the corresponding molecular mass to charge ratio of each component (m/z) in the second. For more detailed analysis further methods can be hyphenated to each other. With each additional application, the selectivity of the system will increase and the data set extends by one more dimensions. Beside the increased resolution power of the common analytical device, it is a challenge to keep the complexity of the apparatus low and to provide, that after each separation, the entirety of the eluents is lead to the next step without merging.

SUMMARY OF THE INVENTION

It is therefore an object of the present invention to provide an improved comprehensive two-dimensional on-line analysis of chemical compounds.

This object is achieved by a method according to claim 1 and/or a device according to claim 10 of the present invention.

Accordingly a method for repetitive chemical analysis of a gas flow is provided, wherein said gas flow consists of a carrier gas and gaseous chemical compounds, comprising the following method steps: feeding said gas flow to a gas chromatographic separation column by means of a feeding device; collecting at least a part of said gaseous chemical compounds for a defined time period by means of a thermally based collecting device which is coupled to said gas chromatographic separation column and/or said feeding device; releasing said collected gaseous chemical compounds in a temporally focused manner by means of said thermally based collecting device; separating said released gaseous chemical compounds by means of said gas chromatographic separation column; and analyzing said separated gaseous chemical compounds by means of an analyzer.

Further, a device for performing repetitive chemical analysis of a gas flow is provided, wherein said gas flow consists of a carrier gas and gaseous chemical compounds, comprising: a gas chromatographic separation column; a feeding device for feeding said gas flow to said gas chromatographic separation column; a thermally based collecting device which is coupled to said gas chromatographic separation column and/or said feeding device for collecting at least a part of said gaseous chemical compounds for a defined time period and for releasing said collected gaseous chemical compounds in a temporally focused manner, wherein said released gaseous chemical compounds are separable by means of said gas chromatographic separation column; and an analyzer for analyzing said separated gaseous chemical compounds.

The basic idea of the present invention is to use the thermally based collecting device to interrupt the continuous flow of chemical compounds to the analyzer and to subsequently release the collected compounds in a timely focused manner to a gas chromatographic separation column, wherein the separation column separates the compounds chronologically according to its retention time in the separation column. Consequently, it is possible to increase the separation power, for example of isobaric compounds by separating this compounds chronologically by means of the gas chromatographic separation column and to increase the sensitivity of the analysis method by enriching the chemical compounds by means of the collecting device.

Advantageous embodiments and configurations of the invention result from the dependent claims and from the description in synopsis with the figures of the drawing.

In an advantageous embodiment of the present invention said step of analyzing said separated gaseous chemical compounds is performed by means of an ionizing analysis method, in particular a mass spectrometry method, an ion mobility spectrometry method, a photoionization method and/or a resonance-enhanced-multi-photon-ionization method, wherein said ionizing analysis method uses a non-coherent electron beam pumped rare gas excimer light source, a non-coherent light source and/or a coherent light source for ionizing said gaseous chemical compounds. This enables a separation of the chemical compounds according to its molecular masses.

In another advantageous embodiment of the present invention a further step of detecting a retention time of said separated gaseous chemical compounds in said gas chromatographic separation column by means of a detector is provided. This extends the results of the analysis to a further dimension.

In another advantageous embodiment of the present invention said gas flow is sucked through said feeding device, said collecting device and/or said gas separation column by a vacuum which is applied by a vacuum of said analyzer and/or by a vacuum which is applied by an auxiliary vacuum pump. Thereby, a pressurized carrier gas is dispensable which simplifies the method and the device, respectively.

In another advantageous embodiment of the present invention said step of collecting at least a part of said gaseous chemical compounds is performed by reducing a temperature at least in a section of said gas chromatographic separation column and/or said feeding device. This enables an enrichment of the chemical compounds by condensing the compounds at an inner wall of the separation column and/or the feeding device due to the reduced temperature.

In another advantageous embodiment of the present invention a further step of thermal decomposing an analyte into said gaseous chemical compounds is provided, in particular by means of a device for thermoanalysis which is coupled to said feeding device. This enables an evolved gas analysis which expands the application area of the method and/or the device significantly.

In another advantageous embodiment of the present invention said step of analyzing said separated gaseous chemical compounds involves a soft ionization method, in particular a chemical ionization, a photo-ionization and/or a field ionization. This prevents a fragmentation of the chemical compounds during ionization which allows a direct molecular profiling of the chemical compounds.

In another advantageous embodiment of the present invention said step of analyzing said separated gaseous chemical compounds is performed by means of a hard ionization method and a soft ionization method which are used alternating for ionizing said gaseous chemical compounds, wherein said alternating frequency is for example between 1000 HZ and 0.01 Hz, in particular between 100 Hz and 0.01 Hz. This allows on the one hand a direct molecular profiling of the compounds and on the other hand enables to obtain a so-called molecular fingerprint of the fragmented the chemical compounds.

In another advantageous embodiment of the present invention before said step of separating said released gaseous chemical compounds by means of said gas chromatographic separation column said carrier gas is exchanged by a further carrier gas, in particular a rare gas. This enables to use a carrier gas, for example oxygen which, could damage the gas chromatographic separation column. Through this, it is possible to withdraw a gas sample from ambient air, for example.

In another advantageous embodiment of the present invention said analyzer for analyzing said separated gaseous chemical compounds is an ionizing analyzer, in particular a mass spectrometer, an ion mobility spectrometer, a photo ionizer and/or a resonance-enhanced-multi-photon-ionizier. This enables advantageously a characterization of the chemical compounds according to its molecular masses.

In another advantageous embodiment of the present invention a vacuum of said analyzer and/or a vacuum of an auxiliary vacuum pump is usable for sucking said gas flow through said feeding device, said collecting device and/or said gas chromatographic separation column. Thereby, the set-up of the device is significantly simplified because a pressurized carrier gas is dispensable.

In another advantageous embodiment of the present invention said device further comprises a detector for detecting a retention time of said separated gaseous chemical compounds in said gas chromatographic separation column. This enables a characterization of the chemical compounds according to its retention time.

In another advantageous embodiment of the present invention said thermally based collecting device is a modulator, wherein said modulator is for example a two stage cooling modulator which collects at least a part of said gaseous chemical compounds by reducing a temperature at least in a section of said gas chromatographic separation column and/or said feeding device. This enables an enrichment and a temporally focused release of the chemical compounds by simply condensing the compounds due to the reduced temperature.

In another advantageous embodiment of the present invention said feeding device is coupled to a thermoanalysis device, in particular to a simultaneous thermoanalysis thermo balance which thermally decomposes an analyte into said gaseous chemical compounds. This enables a evolved gas analysis in a very comfortable manner.

In another advantageous embodiment of the present invention said device further comprises an accumulation device for adsorbing said gaseous chemical compounds over a defined time period and continuously releasing said adsorbed gaseous chemical compounds over a defined time period. This enables an enrichment of the compounds, whereby the sensitivity of the analysis method is significantly improved.

In another advantageous embodiment of the present invention said device comprises two gas chromatographic separation columns, wherein said two a gas chromatographic separation columns are coupled to each other by a modulator device for a comprehensive multi dimensional gas chromatographically separation of said gaseous chemical compounds. This enables a further dimension in multi dimensional analysis, whereby the application area of the device is significantly improved.

The configurations and embodiments of the invention described above might be combined—if nothing else is explicated—complimentary with each other.

BRIEF DESCRIPTION OF THE DRAWINGS

In the following exemplary embodiments of the invention will be explained in more detail with reference to the figures of the drawing, wherein.

In the figures of the drawing, same structural elements have the same reference numerals if nothing else is explicated.

DETAILED DESCRIPTION OF THE DRAWINGS

Figure 1:
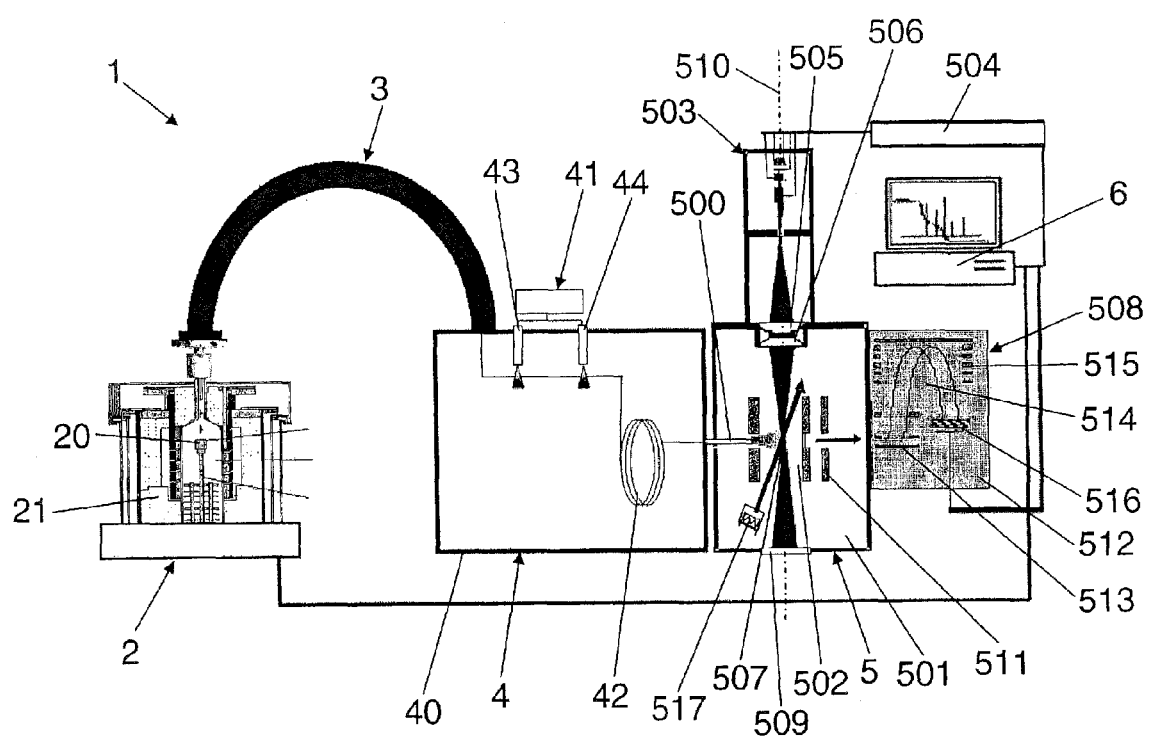
FIG. 1 shows a schematic setup of a preferred embodiment of a device according to the present invention.

FIG. 1 shows a schematic setup of a preferred embodiment of a device according to the present invention.

A device 1 for performing repetitive chemical analysis of a gas flow is illustrated in FIG. 1. The preferred embodiment of the device 1 is usable for example for the investigation of samples like diesel fuel, polymer blends and/or other arbitrary solid, liquid and gaseous substances. For a thermal degradation and decomposition of the sample, for example a thermoanalysis device 2, in particular a simultaneous thermoanalysis (STA) thermo balance 2 is applied. The sample is heated in an crucible 20 of the thermo balance 2, for example in an $Al_2O_3$-crucible 20 preferably from ambient temperature, for example from about 40° C., of a STA furnace 21 to 1000° C. at a heating rate of 10 K $min^{-1}$ in an protective atmosphere which consists for example of $N_2$. During the measurement the sample at least partly evaporates and/or thermally degrades and decomposes into a variety of gaseous chemical compounds. The starting temperature, the end temperature, the heating rate and the kind of protective gas depend on the kind of the sample and are thus just meant exemplary. During the measurement, the protective gas flow through the STA furnace 21 is preferably constant. As results of the STA measurement are obtained, for example, the loss of weight of the sample due to thermal degradation and/or evaporation depending on the preset temperature profile in the furnace 21 and the time and/or the enthalpy difference between a reference and the sample also depending on the preset temperature profile in the furnace 21 and the time.

In an alternative embodiment of the device 1 the sample is not thermally degraded and decomposed to obtain gaseous chemical compounds to analyze but is taken in form of gases directly from ambient air, the breath of humans or animals. In the case that the sample is taken from the breath of humans or animals the method and/or the device are usable for example to detect diseases which are for example diagnosable by a change in the chemical composition of the breath air. A further way to obtain gaseous samples is to evaporate solid or liquid samples. Preferred methods for evaporating substances are for example laser ablation, thermal evaporation, evaporation due to electric discharge or other evaporation methods known in the art. In another alternative embodiment of the device 1 chemical compounds of a liquid sample or a liquid phase are brought into a gaseous phase by a headspace sampling point, a membrane separator, a thermal evaporation, a spray and/or a drying device, for example a thermo spray or an electrical spray, or by generic methods and applications known in the art. In a further alternative embodiment of the device 1 a continuous, in particular an automated sample supply to the device 1 is provided for process analysis.

A feeding device 3, in particular in form of a heated transfer line 3 enclosing for example a deactivated fused silica capillary, for example having 2.5 m×250 μm inner diameter, connects the thermo balance 2 with an oven 40 of a GC 4. The temperature of the heated transfer line 3 might be set to 250° C. for example. The temperature of the heated transfer line 3 has to be set such high that nearly no retention of the chemical compounds in the deactivated fused silica capillary occurs.

In another preferred embodiment of the device 1 the feeding device 3 consists of a sampling point for example in form of an opening or an intake port at the GC oven 40. Hence, only a short deactivated fused silica capillary is necessary, wherein this silica capillary is arranged in the GC oven 40.

Further, a sample withdrawal directly from the environment is possible. Thereby, a direct "quasi on-line" process analysis of, e.g. industrial process gas streams is possible.

In a further preferred embodiment of the device 1, the feeding device 3 is coupled to a device, in particular to a smoking machine which simulates the smoking process in a standardized, reproducible way. In such a manner, the analysis of chemical compounds released and composed during smoking tobacco is possible.

In a further preferred embodiment of the device 1 an accumulator device is provided for adsorbing and accumulating the gaseous chemical compounds over a longer predetermined time period and continuously releasing the chemical compounds over a defined time period.

The GC oven 40 is preferably equipped with a collecting device 41, for example in form of a two stage liquid $CO_2$ spray modulator 41 for GCxGC measurements. In this embodiment of the device 1 just the GC oven 40 and the modulator device 41 are used. The temperature of the GC oven 40 is preferably set below the temperature of the heated transfer line 3. The fused silica capillary of the heated transfer line 3 is preferably further connected to a fast GC separation column 42, for example BPX 50, 3 m×250 μm ID, 0.25 μm film, 50% Phenyl Polysilphenylene-siloxane, GSE or the same, via a mini union GC capillary connector and is guided through a column holder of the modulator 41 close to a first and a second modulator nozzle 43, 44. Preferably, the GC separation column 42 is a short separation column with a high polarity of the liquid phase. Furthermore, two separation columns 42 can be applied which are preferably coupled to each other by a modulator device for comprehensive multidimensional gas chromatographically separation of the gaseous chemical compounds. Due to its length the GC separation column 42 is preferably coiled in the GC oven 40.

Instead of a $CO_2$-cooled modulator 41, the modulator 41 can be cooled by other cryogens, like nitrogen, hydrogen or the like, fluids, gases, ambient air, peltier elements and/or expansion cooling or the same. Further, the collection and accumulation of the chemical compounds can occur by a vent system. In another preferred embodiment of the device 1, the modulator 41 is for example heated electrically, by a laser light source, heat radiation and/or fluids, for releasing the collected chemical compounds.

During one modulation cycle which lasts for example 30 sec. the GC column 42 and/or the fused silica capillary of the heated transfer line 3 is cooled by the $CO_2$ stream of the modulator 41 at a second stage at the second modulator nozzle 44, while the first $CO_2$ spray of the first modulator nozzle 43 at a first stage is turned off. The eluents of the sample condense at this cold spot at the second modulator nozzle 44 and can thus be concentrated, while the carrier gas, for example $N_2$, sustains the gas flow to an analyzer 5, in particular to a MS 5. After 15 seconds, for example, the first stage turns on at the first modulator nozzle 43, stops the flow of the sample substances from the heated transfer line 3 to the GC column 42 and the second stage at the second modulator nozzle 44 turns off. The analytes are now locked before the first modulator nozzle 43. The chemical compounds of the sample condensed at the second stage at the second modulator nozzle 44 evaporate again due to the elevated temperature of the GC oven 40 and can subsequently be separated by the GC column 42. The temperature of the GC oven 40 is preferably kept constant during one modulation cycle. Figuratively, the modulator 41 works as a lock for the chemical compounds of the sample. The duration of one modulation cycle and therefore the repetition rate of the chromatographically separation/analysis is variable in a wide range and might for example be set to a time period between about 0.2 seconds to several minutes.

Preferably, a retention time of the chemical compounds in the gas chromatographic separation column 42 is captured by a detection device of the GC 4 and is fed to a computer and data acquisition system 6. In an alternative embodiment of the device 1 the carrier gas can be exchanged before entering the GC column 42 by means of a vent system which is arranged in front of or behind the modulator 41. The carrier gas which might be ambient air and might therefore damage the GC column 42 by oxidation is advantageously exchangeable by a further carrier gas like a rare or protective gas, for example He or $N_2$. With this configuration even a very reactive gas like $O_2$ is usable for flushing the furnace 21. By deactivating the modulating function of the modulator 41 and, if necessary increasing the temperature of the GC separation column 42, in particular by means of the GC oven 40, the gas chromatographically separation of the chemical compounds can quasi be offset and a direct on-line measurement by means of the analyzer 5 is possible.

After passing the GC oven 40, the chemical compounds are preferably guided through a gas inlet system 500 into the MS 5. The gas inlet system 500 is for example based on a completely heated 30 cm long aluminium cylinder acting as a short transfer line between the GC oven 40 and an ion source of the MS 5. According to the present embodiment the GC capillary of the GC column 42 is inserted into a vacuum chamber 501 of the MS 5 through a heated steel needle in a centre of the gas inlet system 500 and it is positioned close to an opening of an ion chamber 502 of the MS 5. The pressure of the vacuum chamber 501 is for example set to 1E-4 mbar. This low pressure is preferably used to suck the carrier gas with the chemical compounds from the furnace 21 of the thermo balance 2 through the feeding device 3, the modulator 41 and the GC column 42. Therefore no pressurized carrier gas is necessary to press the chemical compounds trough the device 1. Instead or in addition of the vacuum of the MS 5 an auxiliary vacuum pump can be provided. Thereby, the flow of the gas through the device 1 is regulated by the inner diameter of the capillary of the GC separation column 42, the temperatures of the heated transfer line 3 and/or the GC oven 40 and, if necessary by the output of the auxiliary vacuum pump. Instead of the MS 5 other ionizing analysis methods can be applied, for example an ion mobility spectrometry method, a photoionization method and/or a resonance-enhanced-multiphoton-ionization method.

In the present embodiment of the device 1, photoionization is applied, preferably VUV light with a centre wave length for example at 126 nm (9.8 eV) is used, which is generated by an EBEL 503. The EBEL 503 is controlled by an EBEL controller 504 which is coupled to the computer and data acquisition system 6. For photoionization might further be applied a non-coherent electron beam pumped rare gas excimer light source, a non-coherent light source and/or a coherent light source, for example. Preferably a first and a second lens 505, 506, comprising $MgF_2$ are parts of an interface to continuously irradiate an ionization zone 507 of the MS 5 with VUV intensities of approximately 0.024 mW ($1.5 \times 10^{13}$ VUV photons/s), for example.

The vacuum chamber 501 of the MS 5 is in particular a cubic aluminium vacuum chamber 501 that provides six ports for the connection of the heated gas inlet system 500, an orthogonal acceleration time-of-flight mass spectrometer (oaTOFMS) analyzer 508, the EBEL VUV light source 503, an obverse window 509, a pressure gauge and a turbo molecular pump, which are both not shown in FIG. 1. An ion source of the MS 5, respectively the TOFMS 5 is for example based on a cross beam ion source. An optical axis 510 of the EBEL 503 is flanged orthogonally to an ion lens stack 511 of the TOFMS 5 and to the sample gas stream. The ions generated in the ionization zone 507 are extracted from the ion chamber 502 with an external extracting electrode at a potential of approx. 100 V relative to the ion chamber 502, for example. The extracted ions are transferred through a restricting slit into a TOFMS analyzer vacuum chamber 512. The restricting slit allows maintaining a pressure in the vacuum chamber 501 that is more than one order of magnitude higher than in the TOFMS analyzer vacuum chamber 512. The TOFMS analyzer vacuum chamber 512 is for example based on a compact vacuum chamber of 265×155×75 mm and is also pumped by a turbo molecular pump. The ions are guided and collimated through the restricting slit into an orthogonal TOF ion extractor 513 and enter the TOF extractor 513 at 50 eV, for example, before they are orthogonally extracted into a TOF section 514 by a pulsed voltage of roughly 2 kV. Depending on the mass range, a TOF extraction frequency can be up to 100 kHz, for example. After extraction, the ions are accelerated with typically 2 kV. The oaTOFMS analyzer 508 is in particular equipped with a two-stage grid reflector 515, resulting in an effective flight path length of 430 mm, for example. Thus, the resolution of the oaTOFMS analyzer 508 is increased. After post acceleration the ions are collected by a detector 516. The output signal of the detector 516 is preferably detected simultaneously in two channels of a high-speed (1 Gs/s) analog-to-digital conversion data acquisition card. The two channels can record the detector signal with different amplification in order to extend the single extraction dynamic range of a 8-bit analog-to-digital converter (ADC) from 255 to about 1000. Data collected by the data acquisition card are transferred to the computer and data acquisition system 6 and stored to a hard disc drive. In the preferred embodiment, the TOFMS extraction rate is typically 62.5 kHz and 6250 extractions are co-added on-board to a spectrum which is then transferred to the computer 6. The transfer to the computer 6 takes less than 300 μs during which the acquisition must be stopped. This allows for the recording of about 10 spectra per second. The theoretical dynamic range of each spectrum is thus 1000× 6250=$0.62 \times 10^7$. The practical dynamic range is about $10^6$. The board allows for noise suppressed averaging (NSA), where electronic noise of the ADC is greatly suppressed.

For EI ionization electrons from a glowing filament 517 are accelerated to 70 eV, for example, crossing the ionization zone 507. Switching between the two ionization methods (EI and SPI) in the present embodiment might be performed manually within some seconds. In an alternative embodiment of the device 1, modified electronics are used to switch, which are able to switch within some microseconds, wherein the alternating frequency is preferably between 1000 and 0.01 Hz, in particular between 100 and 0.01 Hz.

The gaseous chemical compounds can therefore be characterized by the retention time as well as by the signals of the ion detecting system in such a way that a comprehensive two-dimensional separation of the chemical compounds occurs.

Figure 2:
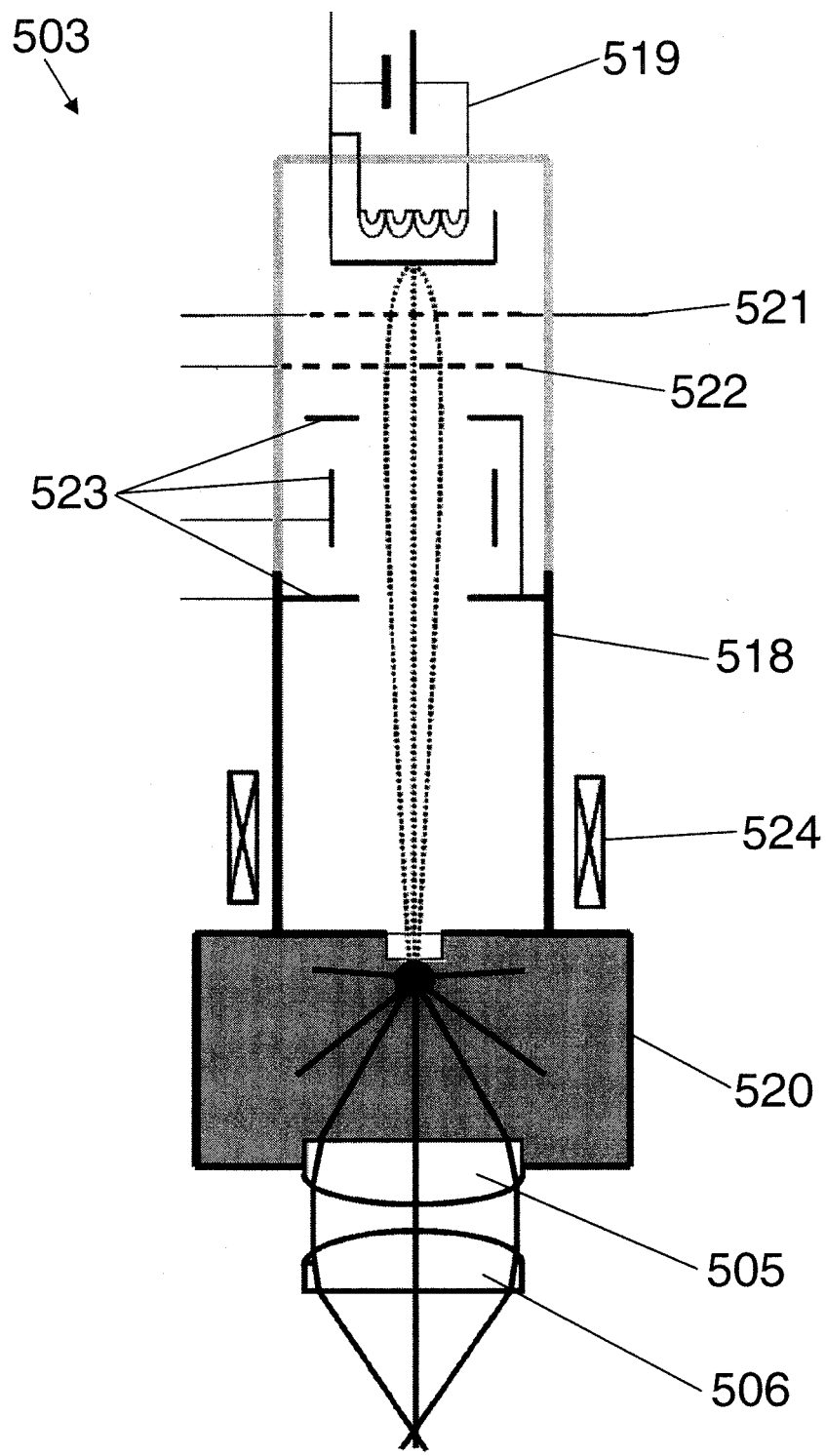
FIG. 2 shows a schematic cross-sectional view of an EBEL light source according to a preferred embodiment of the present invention.

FIG. 2 shows a schematic cross-sectional view of an EBEL light source according to the present invention.

The EBEL light source 503 comprises a vacuum chamber 518 with a glow cathode 519 arranged in the vacuum chamber 518 and a gas chamber 520 which is attached to the vacuum chamber 518 and which comprises a rare gas like Kr or Ar. The gas chamber 520 is separated from the evacuated vacuum chamber 518 by an entry foil. The EBEL 503 further comprises the first and the second lens 505, 506 which comprise $MgF_2$, for example, and which are arranged on a front side of the gas chamber 520, a first and a second acceleration mesh 521, 522 which are arranged inside of the vacuum chamber 518 in front of the glow cathode 519, an electrostatic lens system 523 and a steering magnet 524.

The glow cathode 519 emits electrons into a vacuum of the vacuum chamber 518 in a continuous or pulsed manner. The electrons are accelerated by the first and the second acceleration mesh 521, 522 in direction to the gas chamber 520 and are subsequently focused by the electrostatic lens system 523 and the steering magnet 524. The electrons enter the gas chamber 520 through the entry foil and activate the atoms of the rare gas. The activated rare gas atoms subsequently drop back in its initial inactivated state under emission of ultraviolet light. Thereby, the wavelength of the emitted ultraviolet light depends on the kind of rare gas being used. The emitted ultraviolet light is focused by the first and the second lens 505, 506.

Figure 3:
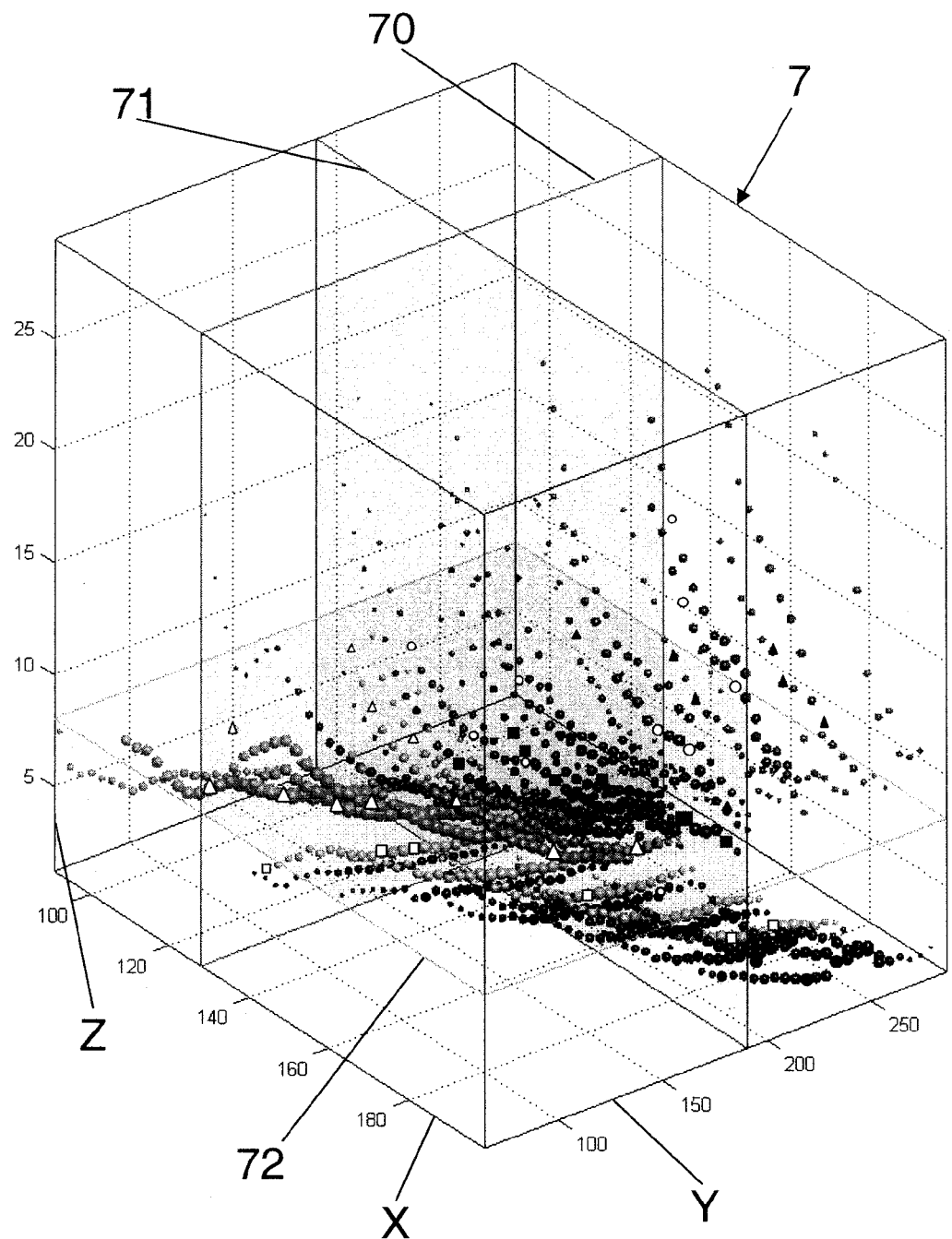
FIG. 3 shows a three-dimensional data cube of an exemplary analysis according to a preferred embodiment of the present invention.
Figure 4:
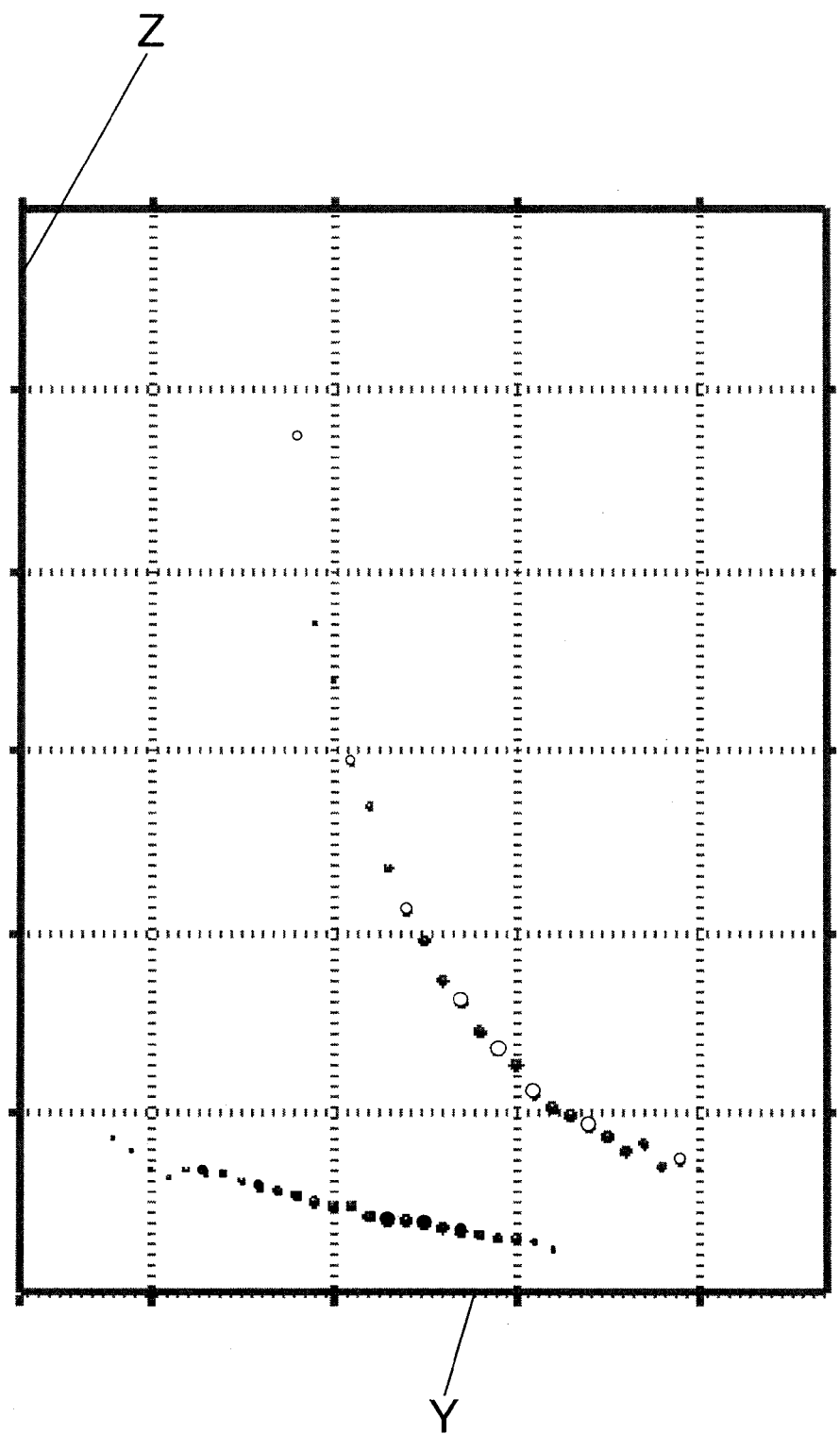
FIG. 4 shows a two-dimensional data sheet of an exemplary layer along an YZ-plane of the data cube according to FIG. 3.
Figure 5:
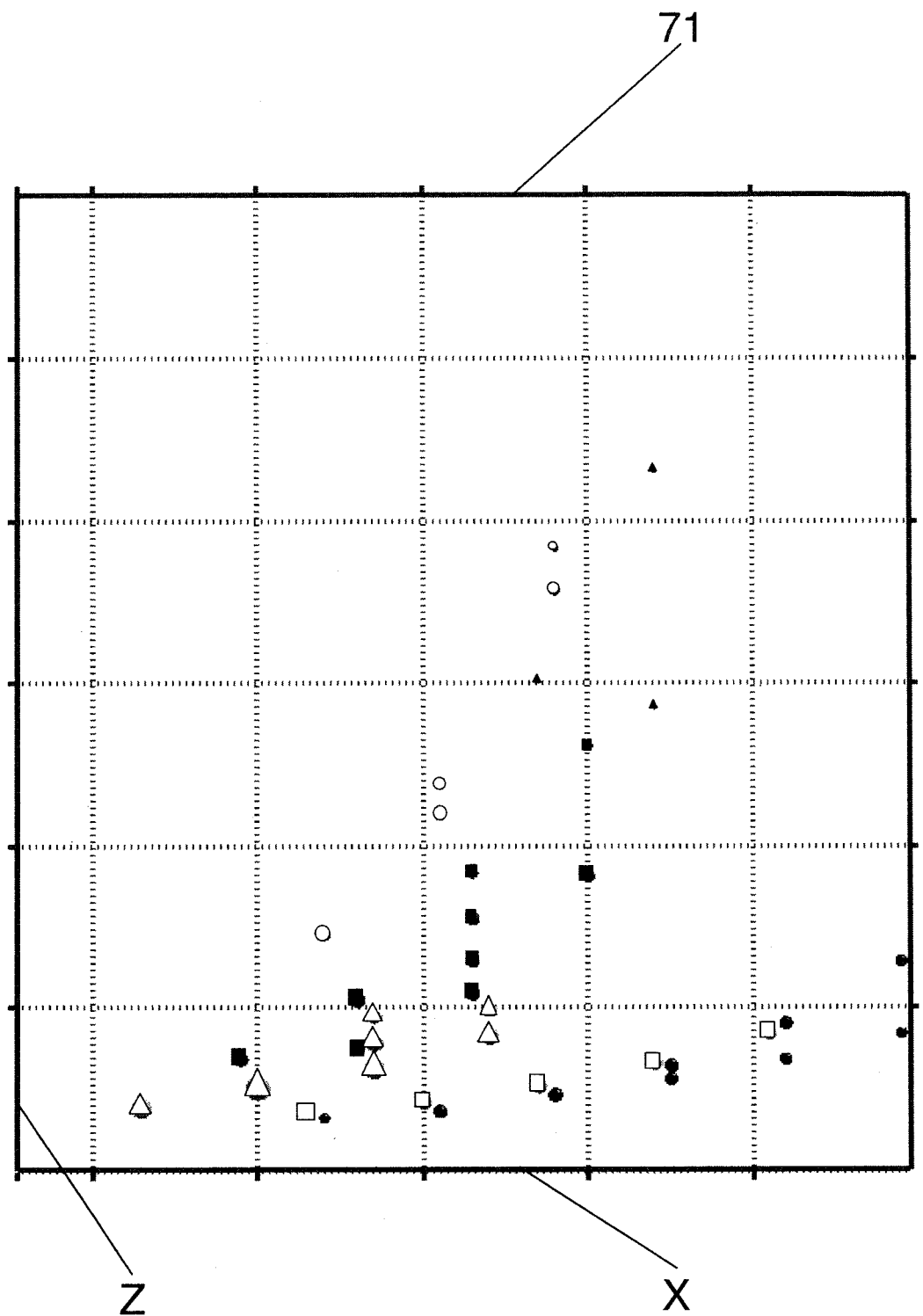
FIG. 5 shows a two-dimensional data sheet of an exemplary layer along an XZ-plane of the data cube according to FIG. 3.
Figure 6:
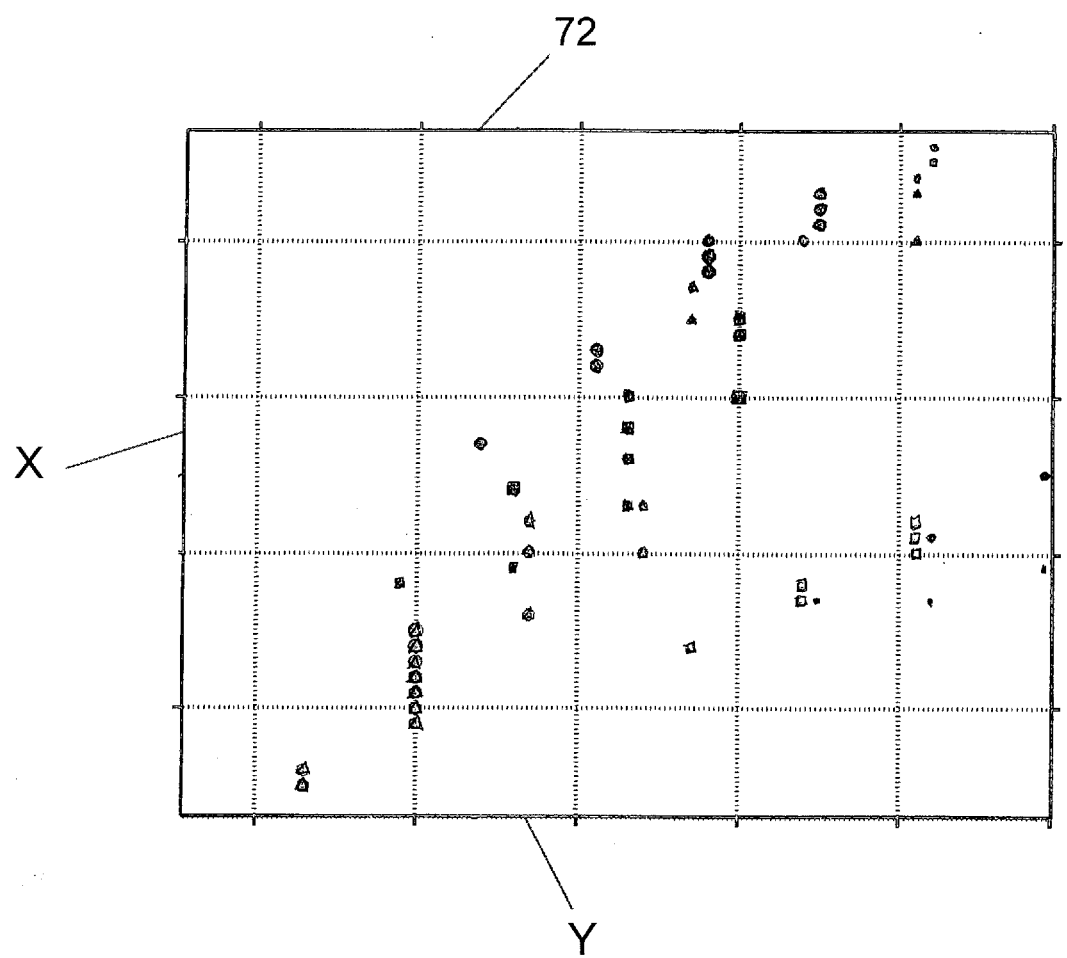
FIG. 6 shows a two-dimensional data sheet of an exemplary layer along an XY-plane of the data cube according to FIG. 3.

FIG. 3 illustrates a three-dimensional data cube of an exemplary analysis according to the present invention, whereas FIG. 4, FIG. 5 and FIG. 6 show two-dimensional data sheets of an exemplary layer along an YZ-, an XZ- and a XY-plane of the data cube according to FIG. 3, respectively.

In the following an exemplary analysis of a Diesel sample according to the present invention is explained, in particular the analysis of isobaric compounds of the sample, namely nonane (128.17 m/z) and naphthalene (128.26 m/z). The homologous series of alkanes and alkylated naphthalenes overlap due to its masses and to the moderate mass resolution of a compact oaTOFMS, which is generally in the range of approx. 850. Therefore, neither identification nor quantification can be provided. With the extension of a TG-SPIMS by a GC separation as described above, the two dimensional surface plot of mass to charge-ratio [m/z] versus Temperature [° C.] provides a data cube 7 including the additional dimension of retention time [s]. FIG. 3 illustrates the 3-D TG-GCx-SPIMS results as a cubic structure, wherein a sample of diesel fuel was heated in the crucible of the thermo balance.

The evolved gases from the TG are first separated by the GC column and hereupon analyzed with the SPIoaTOFMS as explained above. For better clarity only a couple of chemical compounds are picked up to explain the obtained data structure. The different substances injected by the modulator during one modulation cycle are presented as dots, wherein the logarithmic intensity of the MS signals is given as the dots size. The different forms of the dots demonstrate the corresponding chemical classes. Naphthalenes are depicted by an empty circle, alkenes by an empty rectangle, benzenes by an empty triangle, alkanes by a filled circle, indanes by a filled rectangle and acenaphtenes by a filled triangle.

The three axes of the cube 7 are defined by m/z as X, the temperature of the TG-furnace as Y and the retention time of the eluents as Z. For detailed investigation different slides 70, 71, 72 of the cube 7 can be utilized as shown in FIGS. 4 to 6.

FIG. 4 represents the YZ-slide 70 for one mass to charge ratio (e.g. 128 m/z), where the Y-axis is the furnace temperature and the Z-axis is the retention time. The YZ-slide 70 represents the serial sequence of modulated re-injections at different temperatures of the TG-furnace. There are obviously two different compounds with m/z=128, namely nonane (filled circle) and naphthalene (empty circle) that overlap in the m/z dimension. Due to the major polarity of naphthalene compared to nonane, the retention times vary from each other and these two isobaric substances can be clearly separated with the presented setup. The naphthalene curve runs above the nonane curve due to its higher polarity. However, with the programmed temperature ramp of the GC oven the retention time differences decrease to higher oven temperatures. As already mentioned above, with the adoption of the modulator, eluents are refocused and re-injected every 30 seconds (modulation cycle) which is equivalent to a temperature rise of the TG-furnace of respectively 5° C. (at a heating rate of the TG of 10 K/min).

FIG. 5 illustrates the XZ-slide 71 which represents one injection of the modulator at a specific temperature, e.g. T=190° C. It shows the separation in two dimensions due to the m/z ratio as X-axis of each substance and the respective retention time as Z-axis. The distribution of the molecules which depends on the chemical class of the molecules and which is similar to that of a GCxGC, is clearly provided. Due to the various polarities of the substances, isobars as well as some isomers can be separated. To verify whether two separated molecules belong to the same class (isomers) or whether the molecular formula differs (isobars), the m/z-slide 71 can be used. The variation of the retention times in this slide 71 is related to the GC oven temperature and is unequal for different molecular classes. Consequently, the retention behavior of each substance can be monitored and utilized to determine the molecular class relation. For thermal analysis, the TG and DTG curves represent the change of the sample mass due to the temperature rise. With the setup of the present invention, the TG and the DTG curves can be correlated to a sequence of two dimensional separation slides. Each slide represents one re-injection of the sample by the modulator to the GCxSPIMS device. That means that for every change of the sample mass, a clearer evolved gas composition is given by a two dimensional slide, whereas TG-SPIMS provides only a mass spectrum. Therefore, this depiction is very informative one regarding thermal decomposition analysis at any temperature of interest. Depending on the sample nature, TG can also be regarded as a separation technique in very special cases. In general, samples with components having a boiling temperature less than the decomposition temperature of the samples, e.g. fuels or oils, show a temperature dependent volatility and can be separated by distillation.

This behaviour can be reflected in the retention time-layer shown by the XY-slide 72 of FIG. 6, wherein the X-axis is the m/z separation and the Y-axis is the temperature of the TG-furnace and therefore the separation due to boiling point of the components. Compounds with a higher boiling temperature are in the range of higher temperatures, whereas highly volatile substances like benzene and alkylated benzenes are located in the lower temperature regions.

Referring again to the cubic structure 7 of FIG. 3, different retention time intervals can be used to preselect the sample components due to the polarity of the components, and to characterize the components using the m/z ratio and the boiling point information according to the compound location in the retention time layer. Sample substances with a high polarity are located at the top of the data cube 7, whereas less polar compounds are positioned at the bottom. A summation of all retention time layers will lead to the two dimensional contour plot as it is the case using TG-SPIMS and provide a simplified picture of the sample composition.

Figure 7A:
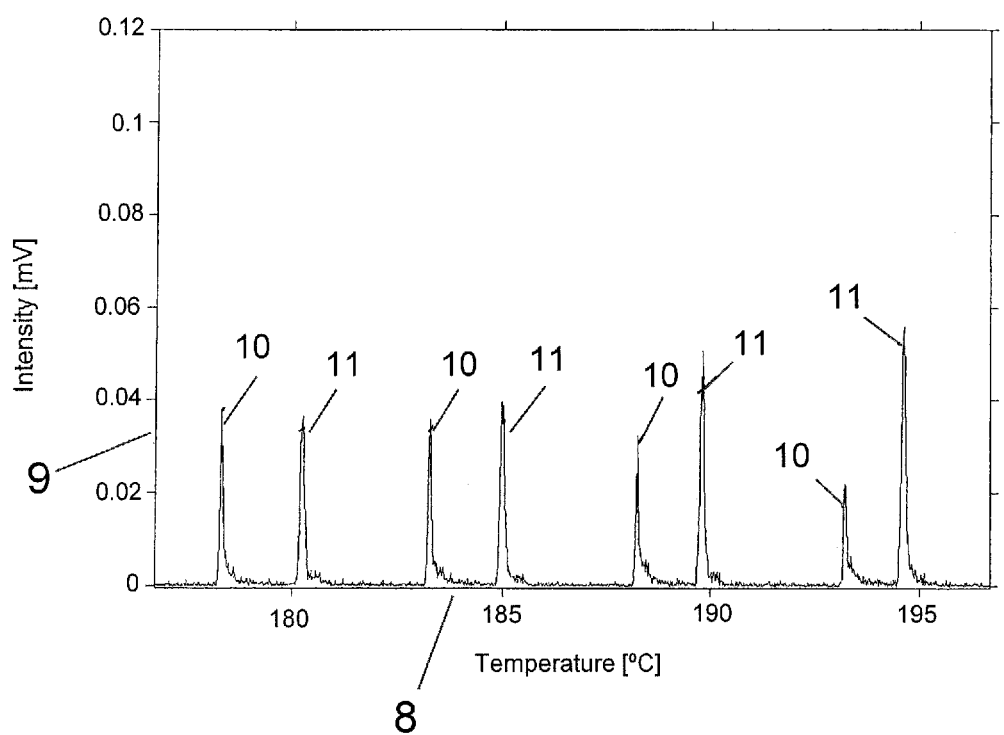
FIGS. 7A-C exemplary visualize three ion traces of chemical compounds analysed according to a preferred embodiment of the method of the present invention.
Figure 7B:
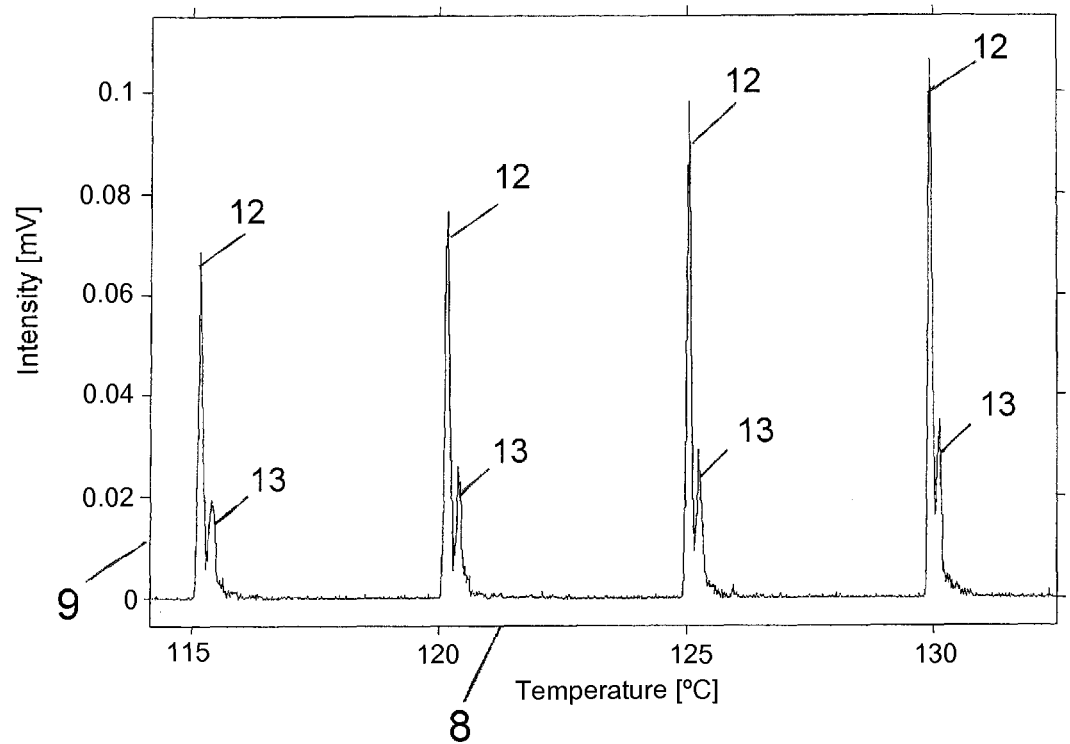
Figure 7C:
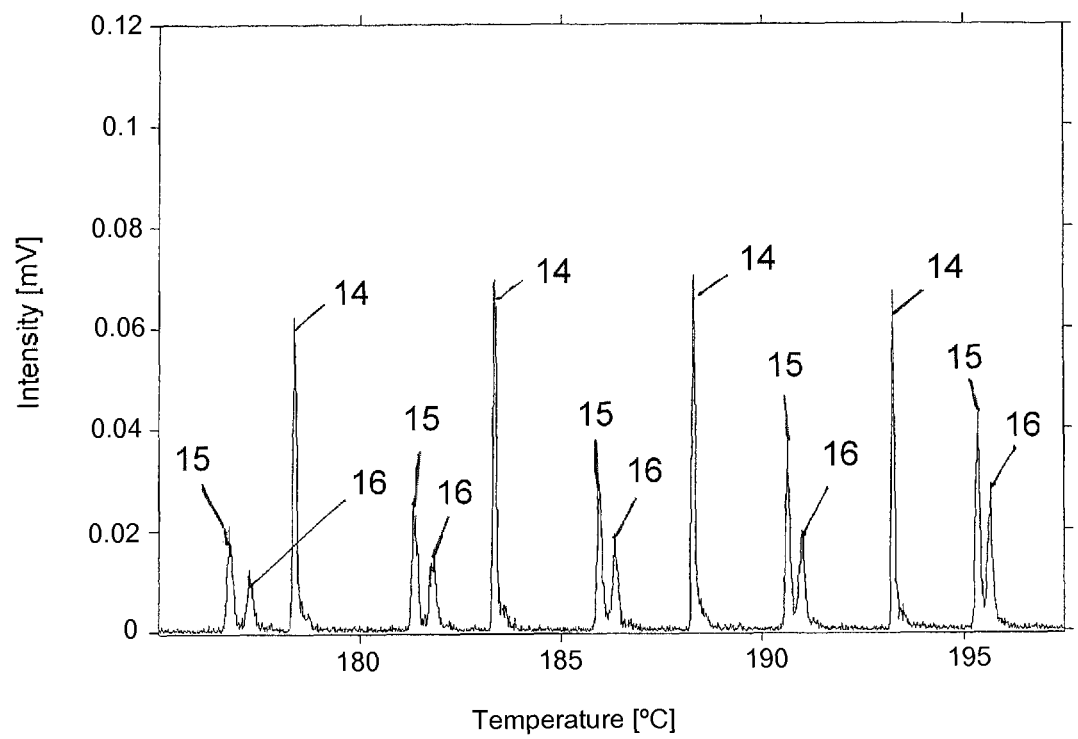

FIGS. 7A-C exemplary visualize three ion traces of chemical compounds analysed according to the method of the present invention.

Regarding ion traces, separation of isobars and isomers can also be investigated. FIGS. 7A-C show three ion traces for mass to charge ratios m/z=106, m/z=128 and m/z=142. In FIGS. 7A-C the horizontal axis 8 is the temperature [° C.] axis, whereas the vertical axis 9 is the intensity axis [mV]. Since it is well known for BPX 50 seperation columns, ethyl benzene, o-xylene and p-xylene show a quite similar retention behavior which, depending to the column lengths, can lead to co-elution of these compounds. In contrast, the retention time of m-xylene differs clearly.

A peak 10 in FIG. 7A is thereby suggested to be a first obviously overlapping signal of ethyl benzene, o-xylene and p-xylene and a second peak 11 corresponds to m-xylene.

In FIG. 7B, the ion traces of nonane (m/z=128) and naphthalene (m/z=128) are illustrated. This illustration represents a clear separation of the two isobaric compounds. The two peaks 12, 13 during one modulation cycle, which lasts 30 seconds in the described embodiment, can be attributed to nonane as a first peak 12 and to naphthalene as a second peak 13. To verify this positioning, the different boiling points according to the so-called NIST-database (National Institute of Standards and Technology) are usable. Nonane ($T_{boiling}$=423 K) volatilizes earlier compared to naphthalene ($T_{boiling}$=490 K) and shows a decreasing intensity course, whereas naphthalene describes an increasing signal intensity.

Additionally, a comparison to FIG. 7C which contains the ion traces of decane (m/z=142) and two methylated naphthalenes (m/z=142), can lead to the same conclusion. The retention times of the two alkanes, namely nonane and decane with a peak 14, are almost similar due to the low polarity of this compounds, whereas naphthalene and methylated naphthalene, represented by peaks 15, 16 show a higher dislocation due to its major polarity, respectively Due to the retention behavior of the sample compounds, isobaric as well as isomeric molecular structures can be separated and therefore not only an identification but also a quantification can be provided Additional to the improved resolving power of the TG-GCxSPIMS device, the Limit Of Detection (LOD) is also reduced compared to TG-SPIMS. As mentioned above, a summation over all retention times (30 seconds) leads to the same results as can be provided by TG-SPIMS with an according time resolution of 30 seconds. The SPIMS spectrum displays the sample composition during a time interval of 30 seconds. As one modulation cycle for example takes 30 seconds, the concentration of one assayed substance are the same in both, TG-SPIMS and TG-GCxSPIMS, during this time. Using the modulator device, however, involves two effects, which leads to an LOD improvement. Due to the working principle of the modulator, substances are refocused to a sharp plug, which involves the entire sample evaporating during 30 seconds, before they are re-injected into the GC device. Consequently, the sample compounds are concentrated, while the noise level remains constant and, therefore, a lower LOD is reached. Using controlled cold spots is a well known technique for ultra trace analysis at the expense of temporal resolution. Furthermore, as compounds separate along the GC column, the level of so called chemical noise which can be related to sample impurity can be reduced. The superposition of these two effects leads to an improved LOD in case of TG–GC×SPIMS compared to TG–SPIMS.

Therefore, comprehensive MDA using a thermo balance coupled to GC×SPIMS (TG–GC×SPIMS) provides the opportunity to obtain TG relevant data as well as an improved resolution power to separate isobaric molecular structures of complex samples without losing any fraction of the samples. Additionally, this solution is not associated with any extent of the entire measurement time. Just by turning off the VUV light from the EBEL and turning on the electron beam the ionization process can be switched from SRI to EI. Advantages of the used MS are the high TOF repetition rates and the ability to change the ionization method.

Although the present invention is described completely by means of preferred embodiments it is not limited to this embodiments but modifiable in various ways. In Particular, features of the embodiments described before are combinable in arbitrary manner.

The above mentioned materials, dimensions and numerical data are only exemplary and serve to describe the embodiments and improvements of the invention and have no limiting character.

What is claimed is:

1. Method for repetitive chemical analysis of a gas flow, wherein said gas flow consists of a carrier gas and gaseous chemical compounds, comprising the following method steps:
    feeding said gas flow to a gas chromatographic separation column by means of a feeding device;
    collecting at least a part of said gaseous chemical compounds for a defined time period by means of a thermally based collecting device which is coupled to said gas chromatographic separation column and/or said feeding device;
    releasing said collected gaseous chemical compounds in a temporally focused manner by means of said thermally based collecting device;
    separating said released gaseous chemical compounds by means of said gas chromatographic separation column; and
    analyzing said separated gaseous chemical compounds by means of an analyzer.

2. Method according to claim 1, wherein said step of analyzing said separated gaseous chemical compounds is performed by means of an ionizing analysis method, in particular a mass spectrometry method, an ion mobility spectrometry method, a photoionization method and/or a resonance-enhanced-multi-photon-ionization method, wherein said ionizing analysis method uses a non-coherent electron beam pumped rare gas excimer light source, a non-coherent light source and/or a coherent light source for ionizing said gaseous chemical compounds.

3. Method according to claim 2, wherein said step of analyzing said separated gaseous chemical compounds involves a soft ionization method, in particular a chemical ionization, a photo-ionization and/or a field ionization.

4. Method according to claim 2, wherein said step of analyzing said separated gaseous chemical compounds is performed by means of a hard ionization method and a soft ionization method which are used alternating for ionizing said gaseous chemical compounds, wherein said alternating frequency is for example between 1000 HZ and 0.01 Hz, in particular between 100 Hz and 0.01 Hz.

5. Method according to claim 1, wherein a further step of detecting a retention time of said separated gaseous chemical compounds in said gas chromatographic separation column by means of a detector is provided.

6. Method according to claim 1, wherein said gas flow is sucked through said feeding device, said collecting device and/or said gas separation column by a vacuum which is applied by a vacuum of said analyzer and/or by a vacuum which is applied by an auxiliary vacuum pump.

7. Method according to claim 1, wherein said step of collecting at least a part of said gaseous chemical compounds is performed by reducing a temperature at least in a section of said gas chromatographic separation column and/or said feeding device.

8. Method according to claim 1, wherein a further step of thermal decomposing an analyte into said gaseous chemical compounds is provided, in particular by means of a device for thermoanalysis which is coupled to said feeding device.

9. Method according to claim 1, wherein before said step of separating said released gaseous chemical compounds by means of said gas chromatographic separation column said carrier gas is exchanged by a further carrier gas, in particular a rare gas.

10. Device for performing repetitive chemical analysis of a gas flow, wherein said gas flow consists of a carrier gas and gaseous chemical compounds, comprising:
    a gas chromatographic separation column;
    a feeding device for feeding said gas flow to said gas chromatographic separation column;
    a thermally based collecting device which is coupled to said gas chromatographic separation column and/or said feeding device for collecting at least a part of said gaseous chemical compounds for a defined time period and for releasing said collected gaseous chemical compounds in a temporally focused manner, wherein said released gaseous chemical compounds are separable by means of said gas chromatographic separation column; and
    an analyzer for analyzing said separated gaseous chemical compounds.

11. Device according to claim 10, wherein said analyzer for analyzing said separated gaseous chemical compounds is an ionizing analyzer, in particular a mass spectrometer, an ion mobility spectrometer, a photo ionizer and/or a resonance-enhanced-multi-photon-ionizier.

12. Device according to claim 10, wherein a vacuum of said analyzer and/or a vacuum of an auxiliary vacuum pump is usable for sucking said gas flow through said feeding device, said collecting device and/or said gas chromatographic separation column.

13. Device according to claim 10, wherein said device further comprises a detector for detecting a retention time of said separated gaseous chemical compounds in said gas chromatographic separation column.

14. Device according to claim 10, wherein said thermally based collecting device is a modulator, wherein said modulator is for example a two stage cooling modulator which collects at least a part of said gaseous chemical compounds by reducing a temperature at least in a section of said gas chromatographic separation column and/or said feeding device.

15. Device according to claim 10, wherein said feeding device is coupled to a thermoanalysis device, in particular to a simultaneous thermoanalysis thermo balance which thermally decomposes an analyte into said gaseous chemical compounds.

16. Device according to claim 10, wherein said device further comprises an accumulation device for adsorbing said gaseous chemical compounds over a defined time period and continuously releasing said adsorbed gaseous chemical compounds over a defined time period.

17. Device according to claim 10, wherein said device comprises two gas chromatographic separation columns, wherein said two gas chromatographic separation columns are coupled to each other by a modulator device for a comprehensive multidimensional gas chromatographically separation of said gaseous chemical compounds.

\* \* \* \* \*